United States Patent [19]
Cima et al.

[11] Patent Number: 5,869,170
[45] Date of Patent: Feb. 9, 1999

[54] PREPARATION OF MEDICAL DEVICES BY SOLID FREE-FORM FABRICATION METHODS

[75] Inventors: Linda G. Cima; Michael J. Cima, both of Lexington, Mass.

[73] Assignee: Massachusetts Institute of Technology, Cambridge, Mass.

[21] Appl. No.: 464,593

[22] Filed: Jun. 5, 1995

Related U.S. Application Data

[62] Division of Ser. No. 138,345, Oct. 18, 1993, Pat. No. 5,490,962.

[51] Int. Cl.⁶ .................. B32B 3/26; A61F 2/00
[52] U.S. Cl. .................. 428/304.4; 428/305.5; 428/310.5; 428/315.5; 428/317.9; 428/320.2; 428/322.7; 424/422; 424/423; 424/426
[58] Field of Search .................. 424/422, 423, 424/424, 425, 426; 523/113, 114, 115; 428/212, 304.4, 305.5, 313.3, 316.6, 317.1, 317.9, 320.2, 322.2, 322.7, 397, 398, 411.1, 315.5

[56] References Cited

U.S. PATENT DOCUMENTS

| | | |
|---|---|---|
| 4,060,081 | 11/1977 | Yannas et al. . |
| 4,485,097 | 11/1984 | Bell . |
| 4,520,821 | 6/1985 | Schmidt . |
| 4,609,551 | 9/1986 | Caplan . |
| 4,620,327 | 11/1986 | Caplan . |
| 4,787,900 | 11/1988 | Yannas ........................................... 623/1 |
| 4,927,632 | 5/1990 | Wong ...................................... 424/422 |
| 4,985,036 | 1/1991 | Lommen et al. ........................... 623/15 |
| 5,011,692 | 4/1991 | Fujioka et al. ........................... 424/426 |
| 5,059,123 | 10/1991 | Jernberg .................................. 433/215 |
| 5,171,261 | 12/1992 | Noishiki et al. ............................ 623/1 |
| 5,197,985 | 3/1993 | Caplan . |
| 5,204,055 | 4/1993 | Sachs et al. . |
| 5,226,914 | 7/1993 | Caplan . |
| 5,260,009 | 11/1993 | Penn ......................................... 264/40.1 |
| 5,338,772 | 8/1994 | Bauer et al. .............................. 523/115 |
| 5,370,692 | 12/1994 | Fink et al. .................................. 623/16 |
| 5,447,724 | 9/1995 | Helmus et al. ........................... 424/426 |
| 5,460,758 | 10/1995 | Langer et al. ............................ 264/401 |
| 5,466,462 | 11/1995 | Rosenthal et al. ....................... 424/426 |
| 5,510,066 | 4/1996 | Fink et al. ................................ 264/40.1 |

FOREIGN PATENT DOCUMENTS 41 02 259 A1  7/1992  Germany .

OTHER PUBLICATIONS

Boeree, N.R., et al., "Development of a Degradable Composite for Orthopedic Use: Mechanical Evaluation of an Hydroxyapatite–Polyhydroxygutyrate Composite Material," *BioMaterials*, 14 793–796 (1993).

Martin, R.B., et al., "Bone Ingrowth and Mechanical Properties of Coralline Hydroxyapatite One Year After Implantation," *BioMaterials*, 14, 341–348 (1993).

Sachs, et al., "CAD–Casting: Direct Fabrication of Ceramic Shells and Cores by Three Dimensional Printing," *Manufacturing Review*, 52(2), 117–126 (1992).

Vacanti, et al., "Selective Cell Transplantation Using Bioabsorbable Artificial Polymers as Matrices," *Arch. Surg.*, 123, 545–549 (1988).

*Primary Examiner*—Marie Yamnitzky
*Attorney, Agent, or Firm*—Arnall Golden & Gregory, LLP

[57] ABSTRACT

Solid free-form techniques for making medical devices for controlled release of bioactive agent and implantation and growth of cells are described using computer aided design. Examples of SFF methods include stereo-lithography (SLA), selective laser sintering (SLS), ballistic particle manufacturing (BPM), fusion deposition modeling (FDM), and three dimensional printing (3DP). The macrostructure and porosity of the device can be manipulated by controlling printing parameters. Most importantly, these features can be designed and tailored using computer assisted design (CAD) for individual patients to optimize therapy.

12 Claims, 2 Drawing Sheets

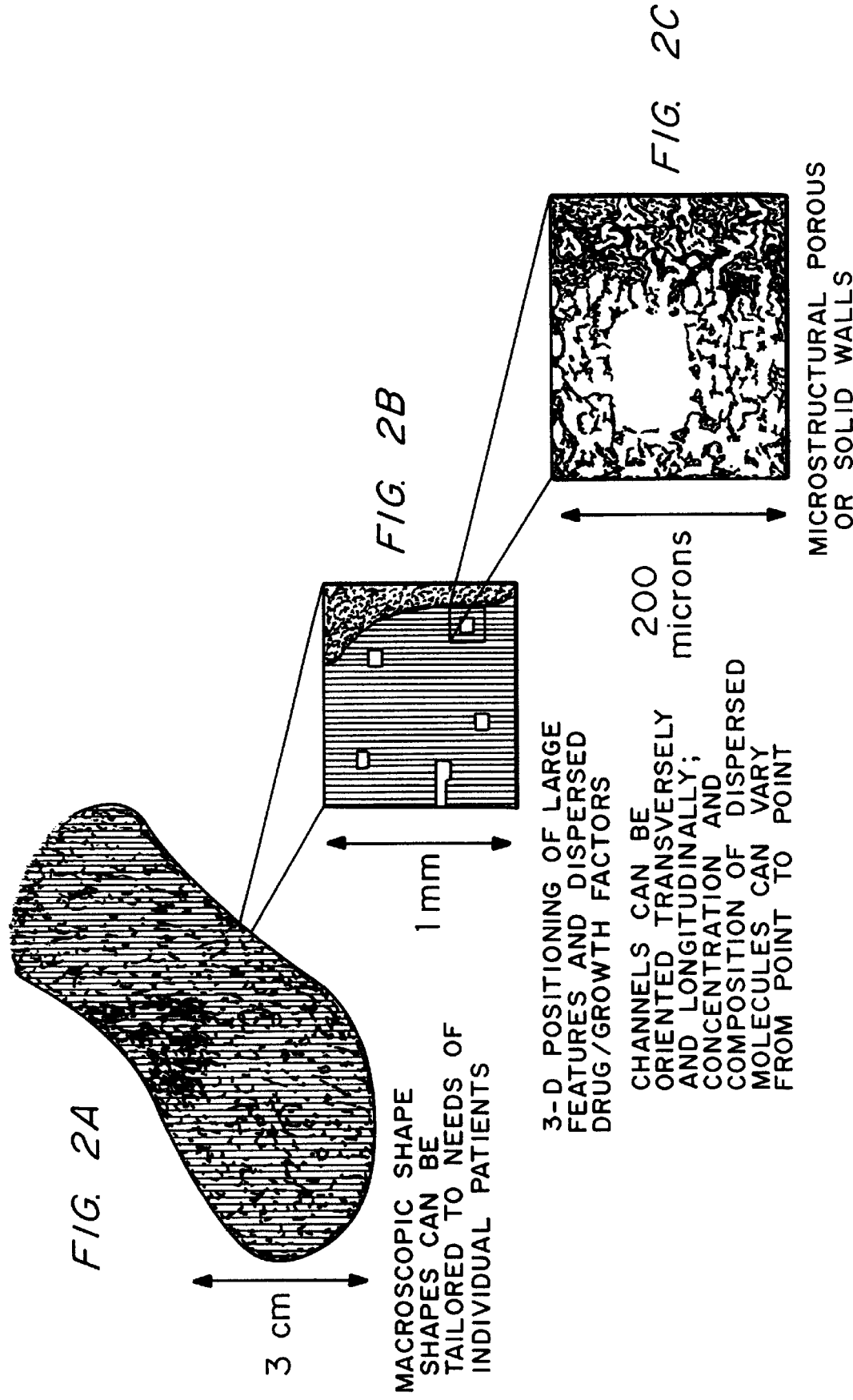

PREPARATION OF MEDICAL DEVICES BY SOLID FREE-FORM FABRICATION METHODS

This is a divisional of application U.S. Ser. No. 08/138,345 filed on Oct. 18, 1993 (now U.S. Pat. No. 5,490,962).

The government has certain rights in this invention by virtue of Grant Number DDM-8913977 awarded by the National Science Foundation.

BACKGROUND OF THE INVENTION

The present invention is generally in the area of methods for formulation of medical devices, in particular using computer aided design in combination with solid free-form fabrication technology.

Many drug regimes require hospitalization or repeated visits because they must be carefully dosed for individual patients or are too complicated for patients to administer themselves. Significant cost savings could be realized if hospital stay and visits were reduced by use of drug delivery devices that accurately deliver drugs at predefined rates for individual patients. Many other drugs which are self-administered have low efficacy because patient compliance is low, even when drugs are supposed to be taken on a simple dosage regime such as once a day.

A number of approaches have been proposed as a means for controlled drug delivery which avoids some of the problems with patient compliance. In most of these cases, this has been achieved by encapsulation of the drug in a polymeric material which releases drug by diffusion, degradation, or a combination of diffusion and degradation, over time. Methods include solvent casting, solvent evaporation, solvent extraction, spray drying, and compression molding. The resulting devices are in the form of tablets, slabs, microparticles, microspheres, and microcapsules. Multiphase release is achieved by encapsulating drug within multiple layers having different release profiles.

One of the problems with the current technology for drug manufacture is the lack of precision and resulting lack of quality control. This in turn causes a lack of precision in the release rates of the encapsulated drug. It also limits the types of multiphasic release to one or two "bursts".

Construction of drug delivery devices which could release drugs according to complex prescribed temporal patterns would increase patient compliance by reducing the number of times a patient must administer the drug. No such methods have been reported at this time, however.

Similarly, a number of approaches have been proposed for construction of synthetic polymeric matrices for growth of cells in vivo, for example, to replace organ function or to provide structural support, i.e., new bone. Such methods have been reported by Vacanti, et al., *Arch. Surg.* 123, 545–549 (1988), U.S. Pat. No. 4,060,081 to Yannas, et al., U.S. Pat. No. 4,485,097 to Bell, and U.S. Pat. No. 4,520,821 to Schmidt, et al. In general, however, the methods used by Vacanti, et al., and Schmidt, et al., involved selecting and adapting existing compositions for implantation and seeding with cells, while the methods of Yannas and Bell were used to produce very specific structures.

Tissue regeneration devices must be porous with interconnected pores to allow cell and tissue penetration; however, factors such as pore size, shape and tortuosity can all affect tissue ingrowth but are difficult to control using standard processing techniques. None of the prior art methods, however, can be used to construct specific structures from biocompatible synthetic polymers, having defined pore sizes, particularly different pore sizes within the same structure, especially in discrete regions of the structure.

It is therefore an object of the present invention to provide methods and compositions made according to complex temporal patterns for use in drug delivery and tissue regeneration.

It is an object of the present invention to provide methods and compositions for making complex medical devices of erodible or erodible and non-erodible materials which can be used as drug delivery devices or for seeding of cells.

It is a further object of the present invention to provide methods that operate with high precision and reproducibility to produce medical devices.

It is a still further object of the present invention to provide bioerodible devices which are structurally stable during erosion.

SUMMARY OF THE INVENTION

Solid free-form fabrication (SFF) methods are used to manufacture devices for controlled release of bioactive agents and for seeding and implantation of cells to form organ and structural components. These methods can be adapted for use with a variety of different materials to create structures with defined compositions, strengths, and densities, through the use of computer aided design (CAD). Examples of SFF methods include stereo-lithography (SLA), selective laser sintering (SLS), ballistic particle manufacturing (BPM), fusion deposition modeling (FDM), and three dimensional printing (3DP). In a preferred embodiment, 3DP is used to precisely position bioactive agent(s) within a release matrix to control the rate of release and allow either a pulsed or constant release profile. In another preferred embodiment, 3DP is used to create a porous bioerodible matrix having interconnected pores or channels, typically between 0.15 and 0.5 mm, which are separated by walls approximately 30 to 100 microns thick, which have an average pore size of approximately 5 to 40 microns.

The macrostructure and porosity of the device can be manipulated by controlling printing parameters, the type of polymer and particle size, as well as the solvent and/or binder. Porosity of the matrix walls, as well as the matrix per se, can be manipulated using SFF methods, especially 3DP. Structural elements that maintain the integrity of the devices during erosion can also be incorporated so that more linear release of incorporated material is obtained. Most importantly, these features can be designed and tailored using computer assisted design (CAD) for individual patients to optimize drug therapy or cell type.

BRIEF DESCRIPTION OF THE DRAWINGS

FIGS. 2A, 2B, and 2C are schematic diagrams of a tissue engineering device: the macroscopic device having a porous internal structure (2A); an expanded excerpt of 2A showing three dimensional position of large features including channels that are oriented transversely and longitudinally, and dispersed drug and growth factors (2B); and an expanded excerpt of 2B showing the microstructure, including porous or solid walls (2C).

DETAILED DESCRIPTION OF THE INVENTION

Figure 1A:
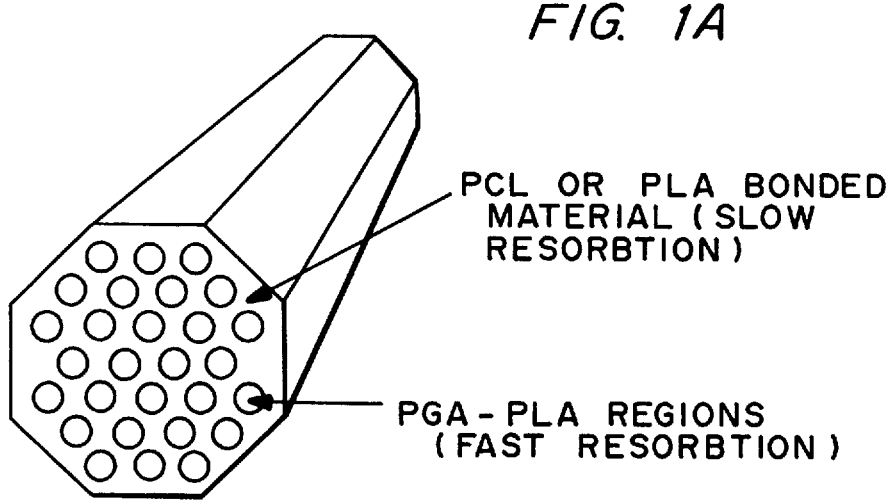
FIG. 1A and 1B are perspective and cross-sectional views, respectively, of polymeric bioactive agent delivery devices made according to the method described herein.

Solid free-form fabrication methods offer several unique opportunities for the construction of medical devices for the delivery of bioactive agents or tissue engineering. Devices for bioactive agent delivery can be constructed with specified bioactive agent composition gradient and structure so that the dosage regimes can be much more complex than currently practiced and tailored for the needs of individual patients. SFF methods can be used to selectively control composition within the build plane by varying the composition of printed material. This means that unconventional microstructures, such as those with complicated porous networks or unusual composition gradients, can be designed at a CAD terminal and built through an SFF process such as 3DP. Complex resorbable or erodible medical devices can also be built which incorporate structural elements to insure the structural integrity of the device during erosion.

Examples of useful SFF processes include:

Three Dimensional Printing (3DP).

3DP is described by Sachs, et al., "CAD-Casting: Direct Fabrication of Ceramic Shells and Cores by Three Dimensional Printing" *Manufacturing Review* 5(2), 117–126 (1992) and U.S. Pat. No. 5,204,055 to Sachs, et al., the teachings of which are incorporated herein. Suitable devices include both those with a continuous jet stream print head and a drop-on-demand stream print head. A high speed printer of the continuous type, for example, is the Dijit printer made and sold by Diconix, Inc., of Dayton, Ohio, which has a line printing bar containing approximately 1500 jets which can deliver up to 60 million droplets per second in a continuous fashion and can print at speeds up to 900 feet per minute. Both raster and vector apparatuses can be used. A raster apparatus is where the printhead goes back and forth across the bed with the jet turning on and off. This can have problems when the material is likely to clog the jet upon settling. A vector apparatus is similar to an x-y printer. Although potentially slower, the vector printer may yield a more uniform finish.

3DP is used to create a solid object by ink-jet printing a binder into selected areas of sequentially deposited layers of powder. Each layer is created by spreading a thin layer of powder over the surface of a powder bed. The powder bed is supported by a piston which descends upon powder spreading and printing of each layer (or, conversely, the ink jets and spreader are raised after printing of each layer and the bed remains stationary). Instructions for each layer are derived directly from a computer-aided design (CAD) representation of the component. The area to be printed is obtained by computing the area of intersection between the desired plane and the CAD representation of the object. The individual sliced segments or layers are joined to form the three dimensional structure. The unbound powder supports temporarily unconnected portions of the component as the structure is built but is removed after completion of printing.

As shown in U.S. Pat. No. 5,204,055, the 3DP apparatus includes a powder dispersion head which is driven reciprocally in a shuttle motion along the length of the powder bed. A linear stepping motor assemble is used to move the powder distribution head and the binder deposition head. The powdered material is dispensed in a confined region as the dispensing head is moved in discrete steps along the mold length to form a relatively loose layer having a typical thickness of about 100 to 200 microns, for example. An ink-jet print head having a plurality of ink-jet dispensers is also driven by the stepping motor assembly in the same reciprocal manner so as to follow the motion of the powder head and to selectively produce jets of a liquid binder material at selected regions which represent the walls of each cavity, thereby causing the powdered material at such regions to become bonded. The binder jets are dispensed along a line of the printhead which is moved in substantially the same manner as the dispensing head. Typical binder droplet sizes are about 15–50 microns. The powder/binder layer forming process is repeated so as to build up the device layer by layer.

While the layers become hardened or at least partially hardened as each of the layers is laid down, once the desired final part configuration is achieved and the layering process is complete, in some applications it may be desirable that the form and its contents be heated or cured at a suitably selected temperature to further promote binding of the powder particles. In either case, whether or not further curing is required, the loose, unbonded powder particles are removed using a suitable technique, such as ultrasonic cleaning, to leave a finished device.

Construction of a 3DP component can be viewed as the knitting together of structural elements that result from printing individual binder droplets into a powder bed. These elements are called microstructural primitives. The dimensions of the primitives determine the length scale over which the microstructure can be changed. Thus, the smallest region over which the concentration of bioactive agent can be varied has dimensions near that of individual droplet primitives. Droplet primitives have dimensions that are very similar to the width of line primitives formed by consecutive printing of droplets along a single line in the powder bed. The dimensions of the line primitive depend on the powder and the amount of binder printed per unit line length. A line primitive of 500 $\mu$m width is produced if an ink jet depositing 1.1 cc/min of methylene chloride is made to travel at 8"/sec over the surface of a PLC powder bed with 45–75 $\mu$m particle size. Higher print head velocities and smaller particle size produce finer lines. The dimensions of the primitive seem to scale with that calculated on the assumption that the liquid binder or solvent needs to fill the pores of the region in the powder which forms the primitive.

Finer feature size is also achieved by printing polymer solutions rather than pure solvents. For example, a 10 wt. % PLC solution in chloroform produces 200 $\mu$m lines under the same conditions as above. The higher solution viscosity prevents slows the migration of solvent away from the center of the primitive.

The solvent drying rate is an important variable in the production of polymer parts by 3DP. Very rapid drying of the solvent tends to cause warping of the printed component. Much, if not all, of the warping can be eliminated by choosing a solvent with a low vapor pressure. Thus, PCL parts prepared by printing chloroform have nearly undetectable amounts of warpage, while large parts made with methylene chloride exhibit significant warpage. It has been found that it is often convenient to combine solvents to achieve minimal warping and adequate bonding between the particles. Thus, an aggressive solvent can be mixed in small proportions with a solvent with lower vapor pressure.

There are two principle methods for incorporation of bioactive agent. In the first method, a layer of dispersed fine polymer powder is selectively bound by ink-jet printing a solvent onto the polymer particles which dissolves the polymer. This process is repeated for subsequent layers to build up the cylinder, printing directly on top of the preceding layer, until the desired shape is achieved. If it is desired to design a constant rate release matrix, the drug is dissolved or dispersed (e.g., micellar) in the solvent, yielding drug dispersed evenly through the matrix. The printing process for this case would then be continued layer by layer until the desired shape was obtained.

In the second method, devices for pulsed release of drugs are prepared by constructing drug-rich regions within the polymer matrix. In this case, multiple printheads are used to deposit drug containing solvent in selected regions of the powder bed. The remaining volume of the desired device is bound with pure solvent deposited by a separate printhead. The printing process is repeated layer by layer to yield a device which gives a pulsed release of drug. For example, a cylindrical device could contain a cylindrical annulus region which is enriched with a drug.

Significant amounts of matter can be deposited in selective regions of a component on a 100 $\mu$m scale by printing solid dispersions or solid precursors through the ink-jet print heads with hundreds of jets can be incorporated into the process. The large number of individually controlled jets make high rate 3DP construction possible.

Stereo-lithography (SLA) and selective laser sintering (SLS).

SFF methods are particularly useful for their ability to control composition and microstructure on a small scale for the construction of these medical devices. The SFF methods, in addition to 3DP, that can be utilized to some degree as described herein are stereo-lithography (SLA), selective laser sintering (SLS), ballistic particle manufacturing (BPM), and fusion deposition modeling (FDM).

Stereolithography is based on the use of a focused ultraviolet (UV) laser which is vector scanned over the top of a bath of a photopolymerizable liquid polymer material. The UV laser causes the bath to polymerize where the laser beam strikes the surface of the bath, resulting in the creation of a first solid plastic layer at and just below the surface. The solid layer is then lowered into the bath and the laser generated polymerization process is repeated for the generation of the next layer, and so on, until a plurality of superimposed layers forming the desired device is obtained. The most recently created layer in each case is always lowered to a position for the creation of the next layer slightly below the surface of the liquid bath. A system for stereolithography is made and sold by 3D Systems, Inc., of Valencia, Calif., which is readily adaptable for use with biocompatible polymeric materials.

SLS also uses a focused laser beam, but to sinter areas of a loosely compacted plastic powder, the powder being applied layer by layer. In this method, a thin layer of powder is spread evenly onto a flat surface with a roller mechanism. The powder is then raster-scanned with a high-power laser beam. The powder material that is struck by the laser beam is fused, while the other areas of powder remain dissociated. Successive layers of powder are deposited and raster-scanned, one on top of another, until an entire part is complete. Each layer is sintered deeply enough to bond it to the preceding layer. A suitable system adaptable for use in making medical devices is available from DTM Corporation of Austin, Tex.

SLA and SLS are similar in that matter is laminated to make three dimensional shapes. The two dimensional profile of each laminate is specified by different methods in the two techniques. Selective photopolymerization of a thin layer of polymer precursor is performed during SLA to define the shape of each layer and bond the layer to previous layers. SLS selectively sinters layers of powder using a laser to define the shape of each layer and to bond to the previous layer. Use of these methods to control composition is limited to one dimensional control since one can only vary the composition of each layer. Nonetheless, these methods can be useful for construction of drug delivery and tissue matrix devices where one dimensional compositional control is all that is desired or where only variation in porosity is desired. Controlled porosity can be built using SLA and SLS simply by specifying the laser path over the layer surface to include only those regions which are to remain in the device.

However, SLA and SLS pose significant material constraints for the construction of drug delivery devices and tissue matrix preforms. SLA is limited to use with a photopolymerizable precursor that yields a biocompatible solid, such as UV or visible light curable acrylic systems used for bioadhesives, or a photo-curable material such as polyethylene oxide (PEO) precursors terminated with photo-crosslinking end groups. This process can be performed in the presence of sensitive biomolecules. Thus, structures can be built that incorporate drugs. Secondly, variation of the laser intensity or traversal speed can be used to vary the cross-link density within a layer so that the properties of the material can be varied from position to position with the part. SLS has the disadvantage that incorporation of sensitive biomolecules is difficult because of the need to locally heat the powder layer so as to sinter it. Nonetheless, highly porous structures can be built with low melting polymers, such as PEO powder. Variation of the laser intensity or traversal speed controls the degree of local densification. Thus, regions where the laser intensity is high or the traversal speed is low will have higher density.

Ballistic particle manufacturing (BPM) and Fusion deposition modeling (FDM)

BPM uses an ink-jet printing apparatus wherein an ink-jet stream of liquid polymer or polymer composite material is used to create three-dimensional objects under computer control, similar to the way an ink-jet printer produces two-dimensional graphic printing. The device is formed by printing successive cross-sections, one layer after another, to a target using a cold welding or rapid solidification technique, which causes bonding between the particles and the successive layers. This approach as applied to metal or metal composites has been proposed by Automated Dynamic Corporation of Troy, N.Y.

FDM, one would use an x-y plotter with a z motion to position an extrudable filament formed of a polymeric material, rendered fluid by heat or the presence of a solvent. A suitable system is available from Stratasys, Incorporated of Minneapolis, Minn.

BPM FDM and 3DP are related in the sense that all three approaches deposit matter in small areas. Thus, they offer the advantage that local composition can be specified and constructed for any desired three dimensional profile. The composition control is only limited by the resolution of the particular apparatus used for construction. FDM builds structures by extruding a fine filament of plastically deformable material through a small nozzle. The nozzle is directed over the built surface by appropriate x, y and z motion control so as to yield the desired three dimensional structure. Similarly, BPM involves motion control of an ink jet print head to deposit matter in the form of small droplets. Appropriate control of where the droplets are printed permits the construction of a desired three dimensional shape. 3DP uses two sources of material: the material that makes up the porous layer and the material that is printed.

Local composition control using FDM and BPM requires the application of multiple printing or extrusion tools. A similar approach can be followed with 3DP by using multiple print-heads. Alternatively, multiple droplets may be printed into the same location when using 3DP to increase the local composition of the species contained in the printed solution.

Porosity control using BPM and FDM can be accomplished using procedures similar to those which can be practiced using 3DP, as described below.

Selection of Polymers

Depending on the processing method, the polymer forming the matrix may be in solution, as in the case of SLA, or in particle form, as in the case of SLS, BPM, FDM, and 3DP. In the first method, the polymer must be photopolymerizable. In the latter methods, the polymer is preferably in particulate form and is solidified by application of heat, solvent, or binder (adhesive). In the case of SLS and FDM, it is preferable to select polymers having relatively low melting points, to avoid exposing incorporated bioactive agent to elevated temperatures.

In the case of 3DP, a polymeric material, preferably in particulate form, or as a porous sheet, is applied to a solid platform on a movable piston for solidification and/or incorporation of bioactive agent. A roller evenly spreads the particles over the platform bed. Solvent and/or binder and bioactive agent is then selectively printed onto the polymer particles. After each layer is "printed", the piston lowers the polymeric material so that the process can be repeated to form the next layer.

The particles can be of any shape, including fibrous or rod shaped, although a more spherical particle will typically flow more smoothly. The particles are preferably in the range of ten microns or greater in diameter, although smaller particles can be used if spread in a liquid medium and allowed to dry in between printings.

A number of materials are commonly used to form a matrix for bioactive agent delivery. Unless otherwise specified, the term "polymer" will be used to include any of the materials used to form the bioactive agent matrix, including polymers and monomers which can be polymerized or adhered to form an integral unit. In a preferred embodiment the particles are formed of a polymer, such as a synthetic thermoplastic polymer, for example, ethylene vinyl acetate, poly(anhydrides), polyorthoesters, polymers of lactic acid and glycolic acid and other $\alpha$ hydroxy acids, and polyphosphazenes, a protein polymer, for example, albumin or collagen, or a polysaccharide containing sugar units such as lactose. The polymer can be non-biodegradable or biodegradable, typically via hydrolysis or enzymatic cleavage. Non-polymeric materials can also be used to form the matrix and are included within the term "polymer" unless otherwise specified. Examples include organic and inorganic materials such as hydoxyapatite, calcium carbonate, buffering agents, and lactose, as well as other common excipients used in drugs, which are solidified by application of adhesive rather than solvent.

Erodible bioactive agent delivery devices are one of the simplest medical devices that can be constructed. These types of bioactive agent delivery devices can be used in an oral or implantable form depending on the desired method for delivering the specific bioactive agent. They differ in the time period over which the bioactive agent is delivered and excipients used in the device construction. Erodible bioactive agent delivery systems are constructed by dispersing the desired bioactive agent in a matrix chosen so that it dissolves or decomposes in the presence of a body fluid. Oral erodible systems, for example, begin to dissolve when they contact digestive fluids. Implantable erodible devices, for example, composed of polyester or polyamides, will slowly hydrolyze in contact with body fluid. In principle, release of the bioactive agent in both cases is controlled both by the rate at which the excipient reacts with the fluid and the rate of bioactive agent diffusion out of the device. This is true only if the surface of the device erodes in a uniform manner and its internal structure remains unchanged by prior reaction at the surface.

Photopolymerizable, biocompatible water-soluble polymers include polyethylene glycol tetraacrylate (Ms 18,500) which can be photopolymerized with an argon laser under biologically compatible conditions using an initiator such as triethanolamine, N-vinylpyrollidone, and eosin Y. Similar photopolymerizable macromers having a poly(ethylene glycol) central block, extended with hydrolyzable oligomers such as oligo(d,l-lactic acid) or oligo(glycolic acid) and terminated with acrylate groups, may be used.

Examples of biocompatible polymers with low melting temperatures include polyethyleneglycol 400 which melts at 4°–8° C., PEG 600 melts at 20°–25° C., and PEG 1500 which melts at 44°–48° C., and stearic acid which melts at 70° C.

Other suitable polymers can be obtained by reference to The Polymer Handbook, 3rd edition (Wiley, NY 1989), the teachings of which are incorporated herein.

In the case of devices for delivery of bioactive agents, the material for construction of the devices is selected based on the mechanism of drug transport and the compatibility of their processing technology with the stability of the bioactive agent. A preferred material is a polyester in the polylactide/polyglycolide family. These polymers have received a great deal of attention with respect to drug delivery and tissue regeneration for a number of reasons. They have been in use for over 20 years in surgical sutures, are Food and Drug Administration (FDA)-approved and have a long and favorable clinical record. A wide range of physical properties and degradation times can be achieved by varying the monomer ratios in lactide/glycolide copolymers: poly-L-lactic acid (PLLA) and poly-glycolic acid (PGA) exhibit a high degree of crystallinity and degrade relatively slowly, while copolymers of PLLA and PGA, PLGAs, are amorphous and rapidly degraded. Although attempts have been made to develop true surface-eroding polymer, for example, polyanhydrides, the relationship between polymer composition and device properties are very difficult to control in practice by standard fabrication techniques. These problems are avoided using the processing technology described herein.

In the case of polymers for use in making devices for cell attachment and growth, polymers are selected based on the ability of the polymer to elicit the appropriate biological response from cells, for example, attachment, migration, proliferation and gene expression. A number of suitable polymers are known, including many described above with reference to delivery of bioactive agent, for example, poly (lactic acid).

Selection of Binder

Solvents and/or binder are used in the preferred method, 3DP, as well as SLA and BPM.

The binder can be a solvent for the polymer and/or bioactive agent or an adhesive which binds the polymer particles. Solvents for most of the thermoplastic polymers are known, for example, methylene chloride or other organic solvents. Organic and aqueous solvents for the protein and polysaccharide polymers are also known, although an aqueous solution is preferred if denaturation of the protein is to be avoided. In some cases, however, binding is best achieved by denaturation of the protein.

The binder can be the same material as is used in conventional powder processing methods or may be designed to ultimately yield the same binder through chemical or physical changes that take place in the powder bed after printing, for example, as a result of heating, photopolymerization, or catalysis.

The selection of the solvent for the bioactive agent depends on the desired mode of release. In the case of an erodible device, the solvent is selected to either dissolve the matrix or is selected to contain a second polymer which is deposited along with the drug. In the first case, the printed droplet locally dissolves the polymer powder and begins to evaporate. The drug is effectively deposited in the polymer powder after evaporation since the dissolved polymer is deposited along with the drug. The case where both the drug and a polymer are dissolved in the printed solution is useful in cases where the powder layer is not soluble in the solvent. In this case, binding is achieved by deposition of the drug polymer composite at the necks between the powder particles so that they are effectively bound together.

Aggressive solvents tend to nearly dissolve the particles and reprecipitate dense polymer upon drying. The time for drying is primarily determined by the vapor pressure of the solvent. There is a range from one extreme over which the polymer is very soluble, for example, 30 weight percent solubility, which allows the polymer to dissolve very quickly, during the time required to print one layer, as compared with lower solubilities. The degree to which the particles are attacked depends on the particle size and the solubility of the polymer in the solvent. Fine powder is more completely dissolved than powder with larger particle size.

Bioactive agents which can be incorporated.

There are essentially no limitations on the bioactive agents that can be incorporated into the devices, although those materials which can be processed into particles using spray drying, atomization, grinding, or other standard methodology, or those materials which can be formed into emulsifications, microparticles, liposomes, or other small particles, and which remain stable chemically and retain biological activity in a polymeric matrix, are preferred. Bioactive agents also include compounds having principally a structural role, for example, hydroxyapatite crystals in a matrix for bone regeneration. The particles may have a size of greater than or less than the particle size of the polymer particles used to make the matrix.

Examples generally include proteins and peptides, nucleic acids, polysaccharides, nucleic acids, lipids, and non-protein organic and inorganic compounds, referred to herein as "bioactive agents" unless specifically stated otherwise. These materials have biological effects including, but not limited to, anti-inflammatories, antimicrobials, anti-cancer, antivirals, hormones, antioxidants, channel blockers, and vaccines. It is also possible to incorporate materials not exerting a biological effect such as air, radiopaque materials such as barium, or other imaging agents.

Patterns for incorporation of Bioactive Agent

There are two principle methods for incorporation of bioactive agents: as a dispersion within a polymeric matrix and as discrete units within a discrete polymeric matrix. In the first case, the bioactive agent is preferably applied in the polymer particle binder; in the second, the bioactive agent is applied in a non-solvent for the polymer particles.

In the case of SLA, bioactive material to be incorporated is dispersed into the liquid matrix material; in all other cases, bioactive material to be incorporated can be mixed with the particles, although this can result in a significant waste of the material in the case of SLS and 3DP; in these cases it is preferable to incorporate the bioactive material into the solvent or binder.

For example, the devices can be composed of particles of bioactive agent dispersed or embedded in a matrix of degradable polymer, such as PLA, PGA, and their copolymers (PLGAs). Implantation of the device is followed by slow hydrolysis and erosion of the polymer matrix. The release rate of bioactive agent is determined by the erosion rate of the polymer rather than just diffusion. Thus, the drug release rate can be controlled by the distribution of the drug throughout the matrix or by variation of the polymer microstructure so that the erosion rate varies with the position in the device. A drug concentration profile that is periodic with position away from the device surface will, for example, yield a drug release rate that is periodic in time as the polymer is eroded. The same effect could also be achieved by periodic variation in polymer composition or porosity. The devices having these release profiles can be constructed as follows. The devices formed using 3DP consist of horizontal layers, or planes, of polymer and/or bioactive agent, arranged in a vertical plane to create a device. Composition gradients are created by applying a different amount of bioactive agent, or different combinations of bioactive agent, in different layers or within different regions of one or more layers. For example, in a device degrading or releasing from the vertical ends, layer one could consist entirely of polymer. Layer two could have a region of bioactive agent with a concentration of 1 mM; layer three a concentration of 1.2 mM; layer four a concentration of 1.4 mM, until the calculated center of the device is reached, at which point the concentration would begin to decrease. Alternatively, for a device degrading or releasing from the vertical sides of the device, the concentration could be formed radially; i.e., the concentration would increase from the outside of the device inwardly, or vice versa, for constant release over a concentration gradient. Alternatively, one could have a discontinuous concentration gradient, for example, where the device is in the form of a cylinder, where, from the outside inward, the outside vertical wall of the cylinder is polymer, the next layer(s) is bioactive agent alone or in combination with polymer, the next layer(s) is polymer, and the next layer(s) is bioactive agent, so that there is a pulsed release as the device degrades. As discussed above, structural elements can be incorporated into the polymeric matrix to insure the mechanical integrity of the erodible devices.

Incorporation of Structural Elements

Practical application of erodible devices is limited by the mechanical integrity of the device during the course of erosion. Real erodible devices do not decompose by simple surface limited reactions. Rather, the surface and bulk microstructure evolve during the course of erosion and alter the rate at which the drug is delivered. For example, oral erodible devices pit and bread apart, which modifies the surface area exposed to the fluid and changes the rate at which drug is released. Resorbable polymer devices swell before hydrolysis which also causes nonlinear release of the drug.

Structural elements made using the same or different polymeric particles can be designed within the device to provide physical structural support during degradation so as to avoid many of the problems associated with erodible devices. 3DP is used to create structural elements within the device formed by the solidification of the polymer particles, for example, by deposition of areas or regions of a different polymeric material, such as regions of a non-degradable polymer within regions of a degradable polymer.

Control of Porosity in Devices.

Porosity in 3D printed devices may be created either at the level of the feature size (10–20 microns and greater) or at a sub-feature size level. At the level of the feature size, porosity is controlled by where the features are placed, and thus pore size and shape can vary in three dimensions.

Porosity at a subfeature size level can be created in a variety of ways.

(1) Printing of a polymer solution onto a bed of particles which are not soluble in the polymer and which can be subsequently leached by a non-solvent for the polymer. In this case, the polymer which forms the device is printed onto a bed of particles such as salt, sugar, or polyethylene oxide. After the printing process is complete, the device is removed from the powder bed and placed in a nonsolvent for the polymer which will dissolve the particles. For example, polylactic acid in chloroform could be printed onto a bed of sugar particles, and the sugar can subsequently be leached with water.

(2) Printing a polymer solution onto a bed of particles which are partially soluble in the printed solvent. An example is printing a polylactic acid solution onto a bed of polyethylene oxide particles. This procedure may allow interpenetration of PEO into the surface of the PLA and improve surface properties of the final device. Following printing, the PEO can be leached with water.

(3) Printing a polymer solution onto a heated bed of polymer. An example is printing polylactic acid in chloroform onto a bed of PLA particles heated to 100° C. The boiling point of chloroform is 60° C., and it will thus boil on hitting the particle bed, causing a foam to form.

(4) Printing a polymer solution onto a bed containing a foaming agent.

(5) Printing with less aggressive solvents which have only a small solubility for the powder. Only a small amount of polymer is deposited at the necks between the particles leaving much of the original porosity in the powder bed. For example, PCL is only slightly soluble in acetone and acetone has a relatively high vapor pressure. Very little polymer is, therefore, dissolved before the solvent dries. Thus, the necks formed between the particles are small and the porosity of the resulting component is much like that of the original powder bed.

Construction of preforms for tissue engineering.

Regeneration of native tissue structures may occur by stimulation of growth of neighboring, healthy tissue (e.g., healing a defect in bone) or may require transplantation of cells from another site, using either the patient's own tissue or that of a tissue-matched donor (e.g., growth of a new cartilage structure for plastic surgery, replacement of liver). In either case, a device which serves as a scaffold or template to aid the growth of the new tissue is almost always necessary. The device may serve many functions, including: (1) as an immobilization site for transplanted cells, (2) forming a protective space to prevent soft tissue prolapse into the wound bed and allow healing with differentiated tissue, (3) directing migration or growth of cells via surface properties of the device, and (4) directing migration or growth of cells via release of soluble molecules such as growth factors, hormones, or cytokines.

For the three applications described above, as well as for other applications in tissue regeneration which could be envisioned, 3DP offers at least three advantages over current technologies for processing biodegradable polymers: (1) tailored macroscopic shapes, (2) well-defined microstructure, which may include bimodal pore size distribution and directionally oriented pores and channels, and (3) incorporation of growth factors during manufacture in order to provide controlled release of factors at specific sites.

The methods and devices described herein will be further understood by reference to the construction of a cylindrical matrix and bone tissue preform below, although in practice any desired shape could be manufactured.

EXAMPLE 1

Construction of a cylindrical matrix having bioactive agent dispersed throughout the matrix The macrostructure and porosity of the device is designed and manipulated by controlling printing parameters. A layer of fine polymer powder having a particle size less than 20 $\mu$m is spread on a solid support which can be moved away from the printhead as layers are built. The powder is selectively bound by ink-jet printing a solvent or mixture of solvents which dissolves the polymer (e.g., methylene chloride for ethylene vinyl acetate, or chloroform for biodegradable polyesters). This process is repeated for subsequent layers to build up the cylinder: the second layer is printed directly on top of the first, and so on until the cylinder is completed.

To design a constant rate release matrix, the bioactive agent is dissolved or dispersed (e.g., micellar) form in the polymer forming the matrix, so that the bioactive agent is dispersed evenly through the matrix. As in the device described above, the printing process is then continued layer by layer until the desired shape is obtained.

EXAMPLE 2

Construction of a cylindrical matrix having bioactive agent located in discrete regions within the matrix Devices for pulsed release of bioactive agent can be obtained by constructing bioactive agent-rich regions within the polymer matrix. In this case, multiple printheads are used to deposit solvent containing bioactive agent in selected regions of the powder bed. The remaining volume of the desired device is bound with pure solvent deposited by a separate printhead. The printing process is then repeated layer by layer, resulting in, for example, a cylindrical device including a cylindrical annulus region which is enriched in a drug. Drug therapies could be devised with graded delivery of multiple drugs simply by adding multiple printheads.

EXAMPLE 3

Figure 1B:
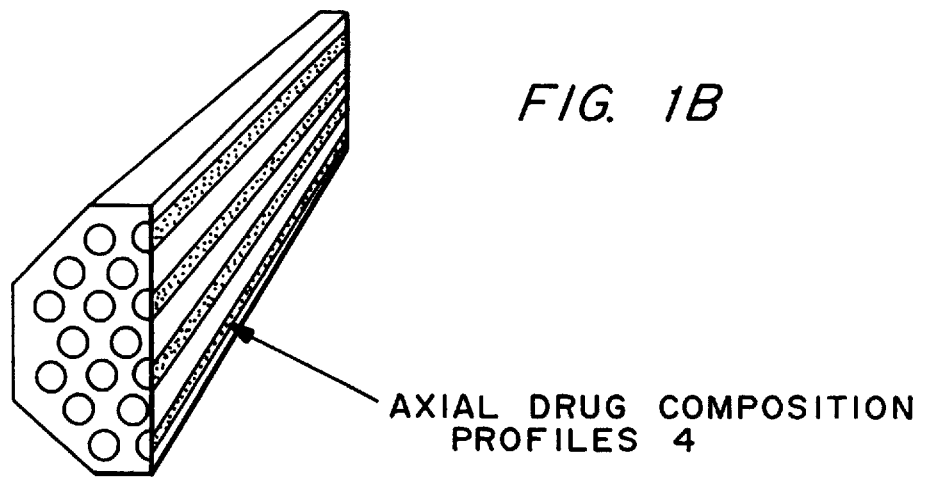

Construction of a cylindrical matrix having structural elements within the matrix A device which can maintain structural integrity during erosion is shown in FIGS. 1A and 1B. The basic design of the device is to surround regions of resorbable polymer containing bioactive agent with a matrix of either nonresorbing or slowly resorbing polymer. This matrix maintains the structural integrity of the resorbing material. The width of the device is chosen so that it is less than five millimeters, so that it can be implanted by a trocar. The regions containing bioactive agent follow the axis of the device and are connected to one or both ends of the device. Thus, resorption of the bioactive agent containing regions will proceed axially from the ends. The width of the bioactive agent containing regions is chosen to be much smaller than the width of the device so that true one-dimensional diffusion will exist along the axis of the device. This feature considerably simplifies the analysis required to determine the proper distribution of bioactive agent along the axis of the device.

The materials needed to construct the device in FIGS. 1A and 1B can be chosen from those currently used in implantable erosive drug delivery devices. This device is constructed by spreading PGA-PLA copolymer powder. The axial filaments, which contain the bioactive agent, are bonded together by printing bioactive agent-chloroform solutions. Drug composition profiles can be created by either printing different bioactive agent solutions into different regions of the filaments or repeated printing of a given solution into regions where high bioactive agent concentration is desired. The matrix around the bioactive agent containing filaments is created by printing solutions of polycaprolactone (PCL) in chloroform. PCL resorbs much slower than the PGA-PLA copolymer powder. Upon drying each layer, the PCL will bind and coat the PGA-PLA powder and dramatically reduce its resorption rate.

Similar fabrication approaches can be used to create oral drug delivery devices. Oral drug delivery devices can be made by printing bioactive agent and digestible polymer solutions into powder composed of acceptable excipient material. Complex composition profiles of the bioactive agent and polymer can be built into the device so that the bioactive agent release rate can be controlled. Polymer-rich walls of a cellular structure could, for example, be built within the device so that their resorption rate controls the release of the bioactive agent held within the cells. The polymer cells simultaneously isolate the bioactive agent from digestive fluids which may inactivate the bioactive agent.

EXAMPLE 4

Construction of a porous matrix for bone regeneration

Three degrees of hierarchy in control of device structure are important, as shown in FIGS. 2A, 2B, and 2C. At the highest level, gross macroscopic shape is important and formation of complex, three-dimensional shapes is essential for many applications, such as replacement of cartilage and bone. The ability to create specific porous shapes in response to individual patient parameters is a goal not yet realized by current processing techniques. At a second level, control of pore or channel size and orientation on the scale of 50 microns to 1 mm is important. For example, in a bone replacement device, it may be advantageous to have a series of large (approximately 200–500 micron) channels oriented anisotropically along the length of the device to encourage rapid growth of large blood vessels from the anastomoses with the native bone, and have smaller pores leading out of these channels for cell growth. It may also be desired to orient these pores in a graded fashion, with more pores on the interior of the device (facing bone) than on the exterior so that prolapse of soft tissue into the bone will be minimized. Another important feature to control at this level of resolution is distribution of soluble factors which might be released from the device to influence cell behavior. For example, in the case of bone, one might want to release bone morphogenic proteins along the side of the device which faces the bone, and release factors which inhibit soft tissue growth (e.g., decorin) along the side which faces soft tissue. Finally, at a third level, the "walls" of the device may themselves be porous on a scale of 1–10 microns. The porosity at this level is uniform throughout the wall.

Modifications and variations of the method and compositions described herein will be obvious to those skilled in the art from the foregoing detailed description. Such modifications and variations are intended to come within the scope of the appended claims.

We claim:

1. An implantable medical device for controlled release of a bioactive agent made using a solid free-form fabrication method to form successive layers of a biocompatible material into a matrix with a defined macroscopic shape and a defined microstructure comprising porous or solid walls, and a bioactive agent selectively distributed within or between the walls of the microstructure to provide constant rate or pulsed controlled release of the bioactive agent, and/or to form a concentration gradient within the matrix.

2. The device of claim 1 wherein the method is ballistic particle manufacturing or fusion deposition modeling comprising applying particulate biocompatible material to a platform and bonding the particles to each other to form a layer with a defined pattern, and repeating the method to form successive layers into a matrix having a desired macroscopic shape and microstructure.

3. The device of claim 1 wherein the method is three dimensional printing, comprising preparing a dispersion of particles formed of a biocompatible material on a platform; and applying a binder or solvent for the particles to the dispersion of particles to form a layer of solidified material with a defined pattern, and repeating the method to form layers into a matrix having a desired macroscopic shape and microstructure.

4. The device of claim 1 wherein the method is selective laser sintering comprising applying particles to a platform and fusing selected areas of the particles with a laser to form a layer of solidified material with a defined pattern, and repeating the method to form sequential layers into a matrix with a desired macroscopic shape and microstructure.

5. The device of claim 1 wherein the method is stereolithography and the biocompatible material is photopolymerizable prepolymer or monomers comprising photopolymerizing selected areas of a bath of photopolymerizable prepolymer or monomers to form a layer of photopolymerized polymer with a defined pattern, and repeating the process to form successive layers into a matrix having a desired macroscopic shape and microstructure.

6. The device of claim 1 wherein the bioactive agent is added to particles used to form the layers of the matrix and is thereby dispersed throughout the matrix.

7. The device of claim 1 wherein the method comprises using a solvent for the bioactive agent that is not a solvent for the biocompatible material, wherein three dimensional printing is used to form discrete regions of bioactive agent within the matrix.

8. The device of claim 1 wherein the biocompatible material used in the solid free-form fabrication method is in the form of particles.

9. The device of claim 1 wherein the biocompatible material is biodegradable polymer.

10. The device of claim 1 wherein the biocompatible material is a non-degradable polymer and forms a porous matrix through which bioactive agent can diffuse out of the device.

11. The device of claim 1 wherein the bioactive agent is present in different areas of the matrix in different concentrations.

12. The device of claim 1 wherein the bioactive agent is incorporated into the matrix so as to result in pulsed release.

* * * * *